(12) United States Patent
Kozhukh et al.

(10) Patent No.: US 9,783,903 B2
(45) Date of Patent: Oct. 10, 2017

(54) ADDITIVES FOR ELECTROPLATING BATHS

(71) Applicant: Rohm and Haas Electronic Materials LLC, Marlborough, MA (US)

(72) Inventors: Julia Kozhukh, Cambridge, MA (US); Zuhra I. Niazimbetova, Westborough, MA (US); Maria Anna Rzeznik, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 750 days.

(21) Appl. No.: 14/098,555

(22) Filed: Dec. 6, 2013

(65) Prior Publication Data

US 2015/0159288 A1    Jun. 11, 2015

(51) Int. Cl.
| | | |
|---|---|---|
| C25D 3/38 | (2006.01) | |
| C25D 3/32 | (2006.01) | |
| C07D 403/12 | (2006.01) | |
| C07D 403/14 | (2006.01) | |
| C07D 239/48 | (2006.01) | |
| C25D 3/58 | (2006.01) | |
| C25D 3/60 | (2006.01) | |
| C25D 7/12 | (2006.01) | |
| C25D 5/02 | (2006.01) | |
| H05K 3/42 | (2006.01) | |

(52) U.S. Cl.
CPC ............ *C25D 3/32* (2013.01); *C07D 239/48* (2013.01); *C07D 403/12* (2013.01); *C07D 403/14* (2013.01); *C25D 3/38* (2013.01); *C25D 3/58* (2013.01); *C25D 3/60* (2013.01); *C25D 5/02* (2013.01); *C25D 7/123* (2013.01); *H05K 3/423* (2013.01)

(58) Field of Classification Search
None
See application file for complete search history.

(56) References Cited

U.S. PATENT DOCUMENTS

| | | | | |
|---|---|---|---|---|
| 3,532,610 | A * | 10/1970 | Du Rose | C07D 293/10 205/294 |
| 3,871,974 | A | 3/1975 | Duchene | |
| 7,128,822 | B2 | 10/2006 | Wang et al. | |
| 7,374,652 | B2 | 5/2008 | Hayashi et al. | |
| 7,384,533 | B2 | 6/2008 | Sierakowski et al. | |
| 7,662,981 | B2 | 2/2010 | Wang et al. | |
| 7,857,961 | B2 | 12/2010 | Hayashi et al. | |
| 7,875,960 | B2 | 1/2011 | Hsu et al. | |
| 8,268,157 | B2 * | 9/2012 | Niazimbetova | C07D 233/02 106/1.26 |
| 2004/0217009 | A1 | 11/2004 | Mikkola et al. | |
| 2004/0249177 | A1 | 12/2004 | Wang et al. | |
| 2007/0012576 | A1 | 1/2007 | Binstead et al. | |
| 2012/0318676 | A1 | 12/2012 | Najjar et al. | |

FOREIGN PATENT DOCUMENTS

| | | | | |
|---|---|---|---|---|
| EP | 1300487 A1 | 4/2003 | | |
| EP | 1371757 A1 | 12/2003 | | |
| EP | 2327814 A1 | 6/2011 | | |
| WO | 2005011758 A2 | 2/2005 | | |
| WO | WO2012117762 | * | 9/2012 | ............ G03F 7/004 |

OTHER PUBLICATIONS

European Search Report for corresponding European Application No. 14 19 6708, dated Apr. 15, 2015.
Averin, A.D., "Amination of 2-chloro- and 2,4-dichloropyrimidines by polyamines," Chemistry of Heterocyclic Compounds, Sep. 1, 2008, pp. 1146-1157, vol. 44, No. 9.
Kobelev, S.M., "Amination of 4,6- and 2,4- dichloropyrimidines with polyamides", Russian Journal of Organic Chemistry, 2010, pp. 1231-1242, vol. 46, No. 8.
Giorgi-Renault, et al, "Heterocyclic quinones. XIII. Dimerization in the series of 5,8-quinazolinediones: synthesis and antitumor effects of bis(4-amino-5,8-quinazolinediones)", 1988, pp. 3933-3947, vol. 36, No. 10.
Yie-Jai Cherng, "Efficient Nucleophilic Substitution Reactions of Pyrimidyl and Pyrazyl Halides with Nucleophiles under Focused Microway Irradiation," Tetrahedron, Oct. 28, 2002, vol. 58, Issue 5, pp. 887-890.
Search report from corresponding Taiwan 103142553 application, dated Oct. 7, 2016.

* cited by examiner

Primary Examiner — Stefanie S Wittenberg
(74) Attorney, Agent, or Firm — John Piskorski

(57) ABSTRACT

Reaction products of halogenated pyrimidines and nucleophilic linker units are included in metal electroplating baths to provide good throwing power. The electroplating baths can be used to plate metal, such as copper, tin and alloys thereof on printed circuit boards and semiconductors and fill through-holes and vias.

4 Claims, No Drawings

ADDITIVES FOR ELECTROPLATING BATHS

FIELD OF THE INVENTION

The present invention is directed to additives for electroplating baths. More specifically, the present invention is directed to additives for electroplating baths which are reaction products of halogenated pyrimidines and nucleopholic linker units which can be used in metal electroplating baths to provide good throwing power.

BACKGROUND OF THE INVENTION

Methods for electroplating articles with metal coatings generally involve passing a current between two electrodes in a plating solution where one of the electrodes is the article to be plated. A typical acid copper plating solution includes dissolved copper, usually copper sulfate, an acid electrolyte such as sulfuric acid in an amount sufficient to impart conductivity to the bath, a source of halide, and proprietary additives to improve the uniformity of the plating and the quality of the metal deposit. Such additives include levelers, accelerators and suppressors, among others.

Electrolytic copper plating solutions are used in a variety of industrial applications, such as decorative and anticorrosion coatings, as well as in the electronics industry, particularly for the fabrication of printed circuit boards and semiconductors. For circuit board fabrication, typically, copper is electroplated over selected portions of the surface of a printed circuit board, into blind vias and trenches and on the walls of through-holes passing between the surfaces of the circuit board base material. The exposed surfaces of blind vias, trenches and through-holes, i.e. the walls and the floor, are first made conductive, such as by electroless metal plating, before copper is electroplated on surfaces of these apertures. Plated through-holes provide a conductive pathway from one board surface to the other. Vias and trenches provide conductive pathways between circuit board inner layers. For semiconductor fabrication, copper is electroplated over a surface of a wafer containing a variety of features such as vias, trenches or combinations thereof. The vias and trenches are metallized to provide conductivity between various layers of the semiconductor device.

It is well known in certain areas of plating, such as in electroplating of printed circuit boards ("PCBs"), that the use of levelers in the electroplating bath can be crucial in achieving a uniform metal deposit on a substrate surface. Electroplating a substrate having irregular topography can pose difficulties. During electroplating a voltage drop typically occurs within apertures in a surface which can result in an uneven metal deposit between the surface and the apertures. Electroplating irregularities are exacerbated where the voltage drop is relatively extreme, that is, where the apertures are narrow and tall. Consequently, a metal layer of substantially uniform thickness is frequently a challenging step in the manufacture of electronic devices. Leveling agents are often used in copper plating baths to provide substantially uniform, or level, copper layers in electronic devices.

The trend of portability combined with increased functionality of electronic devices has driven the miniaturization of PCBs. Conventional multilayer PCBs with through-hole interconnects are not always a practical solution. Alternative approaches for high density interconnects have been developed, such as sequential build up technologies, which utilize blind vias. One of the objectives in processes that use blind vias is the maximizing of via filling while minimizing thickness variation in the copper deposit between the vias and the substrate surface. This is particularly challenging when the PCB contains both through-holes and blind vias.

Leveling agents are used in copper plating baths to level the deposit across the substrate surface and to improve the throwing power of the electroplating bath. Throwing power is defined as the ratio of the through-hole center copper deposit thickness to the copper thickness at the surface. Newer PCBs are being manufactured that contain both through-holes and blind vias. Current bath additives, in particular current leveling agents, do not always provide level copper deposits between the substrate surface and filled through-holes and blind vias. Via fill is characterized by the difference in height between the copper in the filled via and the surface. Accordingly, there remains a need in the art for leveling agents for use in metal electroplating baths for the manufacture of PCBs that provide level copper deposits while bolstering the throwing power of the bath.

SUMMARY OF THE INVENTION

A compound including a reaction product of one or more compounds having formula:

where $R_1$, $R_2$, $R_3$ and $R_4$ are the same or different and are hydrogen; halogen; linear or branched, substituted or unsubstituted $(C_1-C_{10})$alkyl; $-NR_5R_6$ where $R_5$ and $R_6$ are the same or different and are hydrogen or linear or branched, substituted or unsubstituted $(C_1-C_{10})$alkyl; $(C_1-C_{10})$alkoxy; mercaptan; mercapto$(C_1-C_{10})$alkyl; $-NO_2$; $-NO$; nitro$(C_1-C_{10})$alkyl; or $R_3$ and $R_4$ can be taken together with all of their carbon atoms to form a substituted or unsubstituted aryl; with the proviso that at least one of $R_1$, $R_2$, $R_3$ and $R_4$ is a halogen; and one or more compounds having formula:

$$Y_1-R-Y_2 \quad (II)$$

where $Y_1$ and $Y_2$ are the same or different and are chosen from hydrogen, $-NH_2$, $-SH$, $-OH$ or a moiety having formula:

where A is substituted or unsubstituted $(C_5-C_{12})$cycloalkyl or $(C_5-C_{12})$aryl, and R is a moiety having formula:

when $Y_1$ and $Y_2$ are both hydrogen, and B is substituted or unsubstituted $(C_5-C_{12})$cycloalkyl or $(C_5-C_{12})$aryl, or R is a moiety having formula:

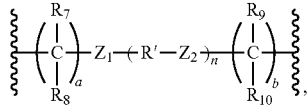  (V)

or R is a moiety having formula:

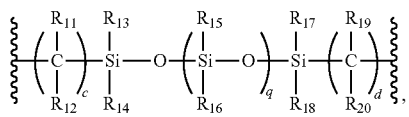  (VI)

and where $Z_1$ and $Z_2$ may be the same or different and are chosen from:

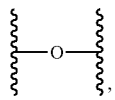  (VII)

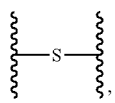  (VIII)

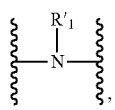  (IX)

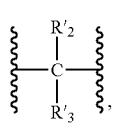  (X)

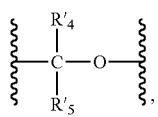  (XI)

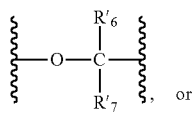  (XII)

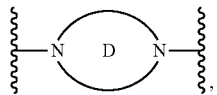  or  (XIII)

where D is substituted or unsubstituted $(C_5-C_{12})$cycloalkyl or $(C_5-C_{12})$aryl, R' is a moiety having formula:

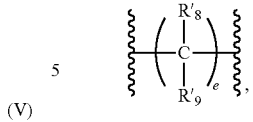  (XIV)

where $R_7$ through $R_{20}$ are the same or different and are chosen from hydrogen, linear or branched $(C_1-C_5)$alkyl, linear or branched amino$(C_1-C_5)$alkyl, hydroxyl, linear or branched hydroxy$(C_1-C_5)$alkyl; $R'_1$ through $R'_7$ are the same or different and are chosen from hydrogen, linear or branched $(C_1-C_5)$alkyl, hydroxyl, linear or branched hydroxy$(C_1-C_5)$alkyl or linear or branched amino$(C_1-C_5)$alkyl; $R'_8$ and $R'_9$ are the same or different and are chosen from hydrogen, linear or branched $(C_1-C_5)$alkyl, hydroxyl, hydroxy$(C_1-C_5)$alkyl or a moiety having formula:

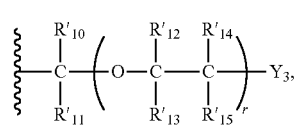  (XV)

where $R'_{10}$ through $R'_{15}$ are the same or different and are chosen from hydrogen or linear or branched $(C_1-C_5)$alkyl, $Y_3$ is $-NH_2$, $-SH$ or $-OH$; a, b, c, d, e, n and q are integers of 1 to 20 and r is 1 to 10.

Metal electroplating compositions include: one or more sources of metal ions, and one or more compounds of a reaction product of one or more compounds of formula:

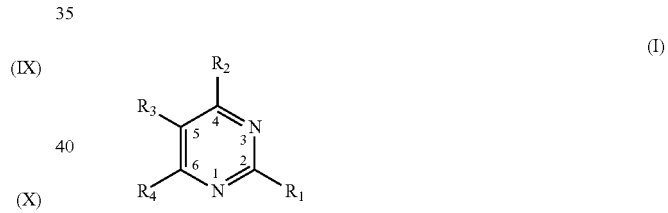  (I)

where $R_1$, $R_2$, $R_3$ and $R_4$ are the same or different and are hydrogen; halogen; linear or branched, substituted or unsubstituted $(C_1-C_{10})$alkyl; $-NR_5R_6$ where $R_5$ and $R_6$ are the same or different and are hydrogen or linear or branched, substituted or unsubstituted $(C_1-C_{10})$alkyl; $(C_1-C_{10})$alkoxy; mercaptan; mercapto$(C_1-C_{10})$alkyl; $-NO_2$; $-NO$; nitro$(C_1-C_{10})$alkyl; or $R_3$ and $R_4$ can be taken together with all of their carbon atoms to form a substituted or unsubstituted aryl; with the proviso that at least one of $R_1$, $R_2$, $R_3$ and $R_4$ is a halogen; and one or more compounds having formula:

$Y_1-R-Y_2$  (II)

where $Y_1$ and $Y_2$ are the same or different and are chosen from hydrogen, $-NH_2$, $-SH$, $-OH$ or a moiety having formula:

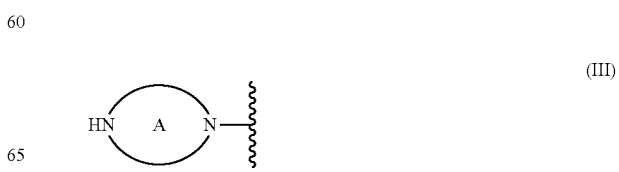  (III)

where A is substituted or unsubstituted $(C_5-C_{12})$cycloalkyl or $(C_5-C_{12})$aryl, and R is a moiety having formula:

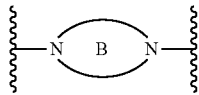
(IV)

when $Y_1$ and $Y_2$ are both hydrogen, and B is substituted or unsubstituted $(C_5-C_{12})$cycloalkyl or $(C_5-C_{12})$aryl, or R is a moiety having formula:

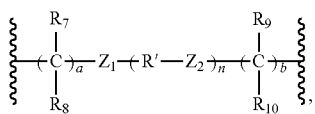
(V)

or R is a moiety having formula:

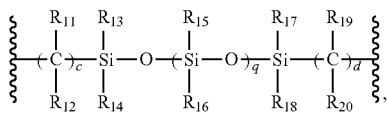
(VI)

and where $Z_1$ and $Z_2$ may be the same or different and are chosen from:

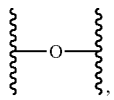
(VII)

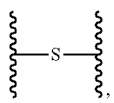
(VIII)

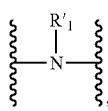
(IX)

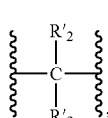
(X)

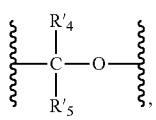
(XI)

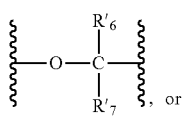
(XII), or

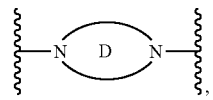
(XIII)

where D is substituted or unsubstituted $(C_5-C_{12})$cycloalkyl or $(C_5-C_{12})$aryl, R' is a moiety having formula:

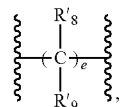
(XIV)

where $R_7$ through $R_{20}$ are the same or different and are chosen from hydrogen, linear or branched $(C_1-C_5)$alkyl, linear or branched amino$(C_1-C_5)$alkyl, hydroxyl, linear or branched hydroxy$(C_1-C_5)$alkyl; $R'_1$ through $R'_7$ are the same or different and are chosen from hydrogen, linear or branched $(C_1-C_5)$alkyl, hydroxyl, linear or branched hydroxy$(C_1-C_5)$alkyl or linear or branched amino$(C_1-C_5)$alkyl; $R'_8$ and $R'_9$ are the same or different and are chosen from hydrogen, linear or branched $(C_1-C_5)$alkyl, hydroxyl, hydroxy$(C_1-C_5)$alkyl or a moiety having formula:

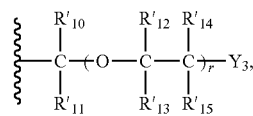
(XV)

where $R'_{10}$ through $R'_{15}$ are the same or different and are chosen from hydrogen or linear or branched $(C_1-C_5)$alkyl, $Y_3$ is $-NH_2$, $-SH$ or $-OH$; a, b, c, d, e, n and q are integers of 1 to 20 and r is 1 to 10.

Methods include contacting a substrate to be metal plated with a metal electroplating composition including: a source of metal ions and one or more compounds of a reaction product of one or more compounds having formula:

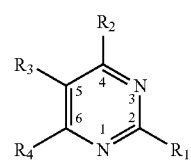
(I)

where $R_1$, $R_2$, $R_3$ and $R_4$ are the same or different and are hydrogen; halogen; linear or branched, substituted or unsubstituted $(C_1-C_{10})$alkyl; $-NR_5R_6$ where $R_5$ and $R_6$ are the same or different and are hydrogen or linear or branched, substituted or unsubstituted $(C_1-C_{10})$alkyl; $(C_1-C_{10})$alkoxy; mercaptan; mercapto$(C_1-C_{10})$alkyl; $-NO_2$; $-NO$; nitro$(C_1-C_{10})$alkyl; or $R_3$ and $R_4$ can be taken together with all of their carbon atoms to form a substituted or unsubstituted aryl; with the proviso that at least one of $R_1$, $R_2$, $R_3$ and $R_4$ is a halogen; and one or more compounds having formula:

$$Y_1-R-Y_2 \quad (II)$$

where $Y_1$ and $Y_2$ are the same or different and are chosen from hydrogen, —$NH_2$, —SH, —OH or a moiety having formula:

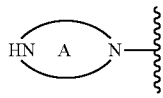
(III)

where A is substituted or unsubstituted $(C_5-C_{12})$cycloalkyl or $(C_5-C_{12})$aryl, and R is a moiety having formula:

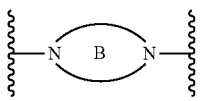
(IV)

when $Y_1$ and $Y_2$ are both hydrogen, and B is substituted or unsubstituted $(C_5-C_{12})$cycloalkyl or $(C_5-C_{12})$aryl, or R is a moiety having formula:

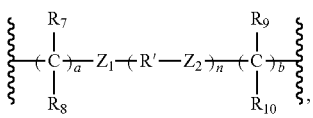
(V)

or R is a moiety having formula:

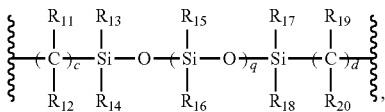
(VI)

and where $Z_1$ and $Z_2$ may be the same or different and are chosen from:

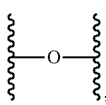
(VII)

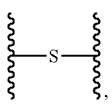
(VIII)

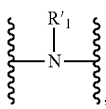
(IX)

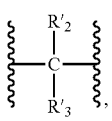
(X)

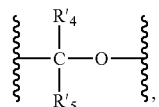
(XI)

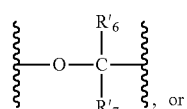
(XII)

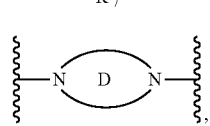
(XIII)

where D is substituted or unsubstituted $(C_5-C_{12})$cycloalkyl or $(C_5-C_{12})$aryl, R' is a moiety having formula:

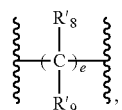
(XIV)

where $R_7$ through $R_{20}$ are the same or different and are chosen from hydrogen, linear or branched $(C_1-C_5)$alkyl, linear or branched amino$(C_1-C_5)$alkyl, hydroxyl, linear or branched hydroxy$(C_1-C_5)$alkyl; $R'_1$ through $R'_7$ are the same or different and are chosen from hydrogen, linear or branched $(C_1-C_5)$alkyl, hydroxyl, linear or branched hydroxy$(C_1-C_5)$alkyl or linear or branched amino$(C_1-C_5)$ alkyl; $R'_8$ and $R'_9$ are the same or different and are chosen from hydrogen, linear or branched $(C_1-C_5)$alkyl, hydroxyl, hydroxy$(C_1-C_5)$alkyl or a moiety having formula:

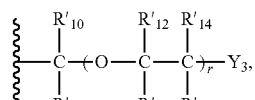
(XV)

where $R'_{10}$ through $R'_{15}$ are the same or different and are chosen from hydrogen or linear or branched $(C_1-C_5)$alkyl, $Y_3$ is —$NH_2$, —SH or —OH; a, b, c, d, e, n and q are integers of 1 to 20 and r is 1 to 10; applying a current; and depositing a metal on the substrate.

The compounds provide metal layers having a substantially level surface across a substrate, even on substrates having small features and on substrates having a variety of feature sizes. The methods effectively deposit metals in blind vias and through-holes such that the metal plating compositions have good throwing power.

DETAILED DESCRIPTION OF THE INVENTION

As used throughout this specification the following abbreviations shall have the following meanings unless the context clearly indicates otherwise: A=amperes; A/dm²=amperes per square decimeter; ° C.=degrees Centigrade; g=gram; mg=milligram; ppm=parts per million;

mol=moles; L=liter, μm=micron=micrometer; mm=millimeters; cm=centimeters; PO=propyleneoxide; EO=ethyleneoxide; DI=deionized; mL=milliliter; Mw=weight average molecular weight; and Mn=number average molecular weight; and v/v=volume to volume. All numerical ranges are inclusive and combinable in any order, except where it is clear that such numerical ranges are constrained to add up to 100%.

As used throughout the specification, "feature" refers to the geometries on a substrate. "Aperture" refers to recessed features including through-holes and blind vias. As used throughout this specification, the term "plating" refers to metal electroplating. "Deposition" and "plating" are used interchangeably throughout this specification. "Halide" refers to fluoride, chloride, bromide and iodide. "Accelerator" refers to an organic additive that increases the plating rate of the electroplating bath. "Suppressor" refers to an organic additive that suppresses the plating rate of a metal during electroplating. "Leveler" refers to an organic compound that is capable of providing a substantially level or planar metal layer. The terms "leveler" and "leveling agent" are used interchangeably throughout this specification. The terms "printed circuit boards" and "printed wiring boards" are used interchangeably throughout this specification. The term "moiety" means a part of a molecule or polymer that may include either whole functional groups or parts of functional groups as substructures. The articles "a" and "an" refer to the singular and the plural.

Compounds are reaction products of one or more halogenated pyrimidine derivatives as disclosed below and one or more nucleophilic linker units. Halogenated pyrimidine compounds have a general formula:

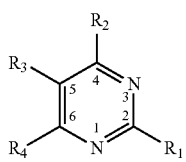
(I)

where $R_1$, $R_2$, $R_3$ and $R_4$ are the same or different and are hydrogen; halogen; linear or branched, substituted or unsubstituted $(C_1-C_{10})$alkyl; $-NR_5R_6$ where $R_5$ and $R_6$ are the same or different and are hydrogen or linear or branched, substituted or unsubstituted $(C_1-C_{10})$alkyl; $(C_1-C_{10})$alkoxy; mercaptan; mercapto$(C_1-C_{10})$alkyl; $-NO_2$; $-NO$; nitro$(C_1-C_{10})$alkyl; or $R_3$ and $R_4$ can be taken together with all of their carbon atoms to form a substituted or unsubstituted aryl; with the proviso that at least one of $R_1$, $R_2$, $R_3$ and $R_4$ is a halogen; preferably, $R_1$, $R_2$, $R_3$ and $R_4$ are the same or different and are hydrogen, halogen, linear or branched, substituted or unsubstituted $(C_1-C_5)$alkyl, $-NH_2$, linear or branched $(C_1-C_5)$alkoxy, mercaptan, $-NO_2$, substituted or unsubstituted phenyl, with the proviso that at least one of $R_1$, $R_2$, $R_3$ and $R_4$ is halogen, preferably chlorine, bromine or iodine. More preferably, $R_1$, $R_2$, $R_3$ and $R_4$ are the same or different and are hydrogen, halogen, $(C_1-C_3)$alkyl, $-NH_2$ or $(C_1-C_3)$alkoxy with the proviso that at least one of $R_1$, $R_2$, $R_3$ and $R_4$ is halogen, more preferably, chlorine or bromine. Preferably, $R_1$ and $R_2$ are halogens where they are ortho and para to both nitrogen atoms.

The one or more nucleophilic linker compounds have a general formula:

$$Y_1-R-Y_2 \quad (II)$$

where $Y_1$ and $Y_2$ are the same or different and are chosen from hydrogen, $-NH_2$, $-SH$, $-OH$ or a moiety having formula:

(III)

where A is substituted or unsubstituted $(C_5-C_{12})$cycloalkyl or $(C_5-C_{12})$aryl and the $(C_5-C_{12})$cycloalkyl groups where A may be monocyclic, spirocyclic, fused rings or bicyclic groups, preferably, A is substituted or unsubstituted $(C_5-C_8)$cycloalkyl or $(C_5-C_{12})$aryl, $Y_1$ and $Y_2$ are the same and are $-NH_2$, $-SH$ or $-OH$, more preferably $Y_1$ and $Y_2$ are the same and are $-NH_2$ or $-OH$, most preferably, $Y_1$ and $Y_2$ are $-NH_2$; and R is a moiety having formula:

(IV)

when $Y_1$ and $Y_2$ are both hydrogen, and B is substituted or unsubstituted $(C_5-C_{12})$cycloalkyl or $(C_5-C_{12})$aryl and the $(C_5-C_{12})$cycloalkyl groups for B may be monocyclic, spirocyclic, fused rings or bicyclic groups, preferably, B is substituted or unsubstituted $(C_5-C_8)$cycloalkyl or $(C_5-C_{12})$aryl, or R is a moiety having formula:

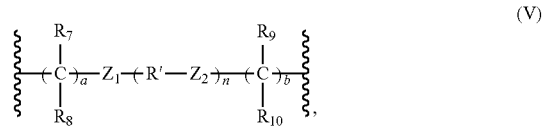
(V)

or R is a moiety having formula:

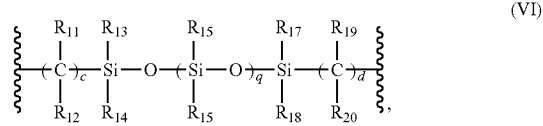
(VI)

where $Z_1$ and $Z_2$ may be the same or different and are chosen from:

(VII)

(VIII)

-continued

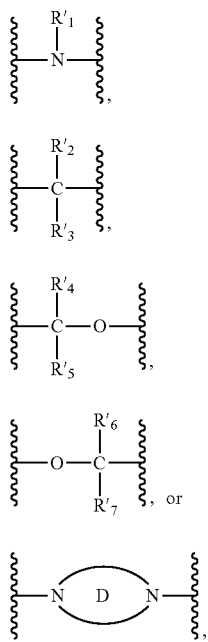

(IX)

(X)

(XI)

(XII)

(XIII)

where D is substituted or unsubstituted $(C_5\text{-}C_{12})$cycloalkyl or $(C_5\text{-}C_{12})$aryl and the $(C_5\text{-}C_{12})$cycloalkyl groups for D may be monocyclic, spirocyclic, fused rings or bicyclic groups, preferably, D is substituted or unsubstituted $(C_5\text{-}C_8)$cycloalkyl or $(C_5\text{-}C_{12})$aryl, $Z_1$ and $Z_2$ are the same or different and are the moieties of formula (VII), (VIIII), (IX), (X), (XI) or (XII), more preferably the moieties of formula (VII), (IX), (XI) or (XII); R' is a moiety having formula:

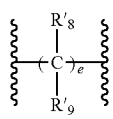

(XIV)

where $R_7$ through $R_{20}$ are the same or different and are chosen from hydrogen, linear or branched $(C_1\text{-}C_5)$alkyl, linear or branched amino$(C_1\text{-}C_5)$alkyl, hydroxyl, linear or branched hydroxy$(C_1\text{-}C_5)$alkyl, preferably, $R_7$ through $R_{20}$ are the same or different and are chosen from hydrogen, $(C_1\text{-}C_3)$alkyl, amino$(C_1\text{-}C_3)$alkyl, hydroxyl or hydroxy$(C_1\text{-}C_3)$alkyl, more preferably, $R_7$ through $R_{20}$ are the same or different and are chosen from hydrogen, $(C_1\text{-}C_3)$alkyl or hydroxyl; $R'_1$ through $R'_7$ are the same or different and are chosen from hydrogen, linear or branched $(C_1\text{-}C_5)$alkyl, hydroxyl, linear or branched hydroxy$(C_1\text{-}C_5)$alkyl or linear or branched amino$(C_1\text{-}C_5)$alkyl, preferably, $R'_1$ through $R'_7$ are the same or different and are chosen from hydrogen, $(C_1\text{-}C_3)$alkyl, hydroxyl, hydroxy$(C_1\text{-}C_3)$alkyl or amino$(C_1\text{-}C_3)$alkyl, more preferably, $R'_1$ through $R'_7$ are the same or different and are chosen from hydrogen, $(C_1\text{-}C_3)$alkyl or hydroxyl; $R'_8$ and $R'_9$ are the same or different and are chosen from hydrogen, linear or branched $(C_1\text{-}C_5)$alkyl, hydroxyl, hydroxy$(C_1\text{-}C_5)$alkyl or a moiety having formula:

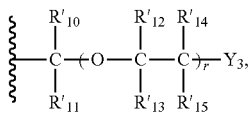

(XV)

where $R'_{10}$ through $R'_{15}$ are the same or different and are chosen from hydrogen or linear or branched $(C_1\text{-}C_5)$alkyl, $Y_3$ is $-NH_2$, $-SH$ or $-OH$, preferably, $Y_3$ is $-NH_2$; a, b, c, d, e, n and q are integers of 1 to 20 and r is 1 to 10; preferably, $R'_8$ and $R'_9$ are the same or different and are hydrogen, $(C_1\text{-}C_3)$alkyl, hydroxyl or the moiety of formula (XV), more preferably, $R'_8$ and $R'_9$ are the same or different and are chosen from hydrogen, $(C_1\text{-}C_3)$alkyl or moiety of formula (XV). Preferably, $R'_{10}$ through $R'_{15}$ are the same or different and are chosen from hydrogen and $(C_1\text{-}C_5)$alkyl; and preferably, a, b, c, d, e, n and q are integers from 1 to 10 and, preferably, r is 1 to 6.

Substituent groups on the A, B, and D variables include, but are not limited to: hydroxyl; linear or branched hydroxy $(C_1\text{-}C_5)$alkyl; mercapto; linear or branched mercapto$(C_1\text{-}C_5)$alkyl; linear or branched $(C_1\text{-}C_5)$alkyl; carboxy$(C_1\text{-}C_5)$alkyl; phenyl; phenyl$(C_1\text{-}C_5)$alkyl; $-N(R'_{16})_t$ where $R'_{16}$ is the same or different and includes, but is not limited to: hydrogen or $(C_1\text{-}C_5)$alkyl and t is an integer of 2 to 3. Preferably, substituent groups are chosen from hydroxyl; hydroxy$(C_1\text{-}C_2)$alkyl; mercapto; mercapto$(C_1\text{-}C_2)$alkyl; $(C_1\text{-}C_5)$alkyl; phenyl and $-N(R'_{16})_t$ where $R'_{16}$ is the same or different and includes, but is not limited to: hydrogen or $(C_1\text{-}C_2)$alkyl and t is an integer of 2 to 3. More preferably, the substituent groups are chosen from hydroxyl; phenyl; $(C_1\text{-}C_5)$alkyl and $-N(R'_{16})_t$ where $R'_{16}$ is the same or different and includes, but is not limited to: hydrogen or methyl and t is an integer of 2 to 3.

In general, the reaction products are prepared by mixing one or more halogenated pyrimidine compounds in an organic solvent, such as an alcohol, with stirring and heating or with stirring at room temperature. One or more nucleophilic linkers are then added dropwise to the mixture of the one or more halogenated pyrimidine compounds and organic solvent with heating and stirring. Heating is typically done in a range of 60° C. to 150° C. This mixture may then be heated for 2 hours to 8 hours followed by bringing the temperature down to room temperature with stirring over 12 hours to 24 hours. The amounts for each component may vary but in general sufficient amount of each reactant is added to provide a product where the molar ratio of the halogenated pyrimidine moiety to the nucleophilic linker moiety ranges from 0.5-1:0.05-2.

The plating composition and method are useful in providing a substantially level plated metal layer on a substrate, such as a printed circuit board. Also, the plating composition and method are useful in filling apertures in a substrate with metal. Also, the metal deposits have good throwing power.

Any substrate upon which metal can be electroplated is useful in the present invention. Such substrates include, but are not limited to: printed wiring boards, integrated circuits, semiconductor packages, lead frames and interconnects. An integrated circuit substrate may be a wafer used in a dual damascene manufacturing process. Such substrates typically contain a number of features, particularly apertures, having a variety of sizes. Through-holes in a PCB may have a variety of diameters, such as from 50 μm to 350 μm in diameter. Such through-holes may vary in depth, such as from 0.8 mm to 10 mm PCBs may contain blind vias having a wide variety of sizes, such as up to 200 μm diameter and 150 μm depth.

Conventional metal plating compositions may be used. The metal plating compositions contain a source of metal ions, an electrolyte, and a leveling agent, where the leveling agent is a reaction product of one or more halogenated pyrimidine compounds of formula (I) with one or more nucleophilic linker compounds of formula (II). The metal plating compositions may contain a source of halide ions, an accelerator and a suppressor. Metals which may be electroplated from the compositions include, but are not limited to: copper, tin and tin/copper alloys.

Suitable copper ion sources are copper salts and include without limitation: copper sulfate; copper halides such as copper chloride; copper acetate; copper nitrate; copper tetrafluoroborate; copper alkylsulfonates; copper arylsulfonates; copper sulfamate; copper perchlorate and copper gluconate. Exemplary copper alkylsulfonates include copper ($C_1$-$C_6$)alkylsulfonate and more preferably copper ($C_1$-$C_3$) alkylsulfonate. Preferred copper alkylsulfonates are copper methanesulfonate, copper ethanesulfonate and copper propanesulfonate. Exemplary copper arylsulfonates include, without limitation, copper benzenesulfonate and copper p-toluene sulfonate. Mixtures of copper ion sources may be used. One or more salts of metal ions other than copper ions may be added to the present electroplating baths. Typically, the copper salt is present in an amount sufficient to provide an amount of copper metal of 10 to 400 g/L of plating solution.

Suitable tin compounds include, but are not limited to salts, such as tin halides, tin sulfates, tin alkane sulfonate such as tin methane sulfonate, tin aryl sulfonate such as tin benzenesulfonate and tin toluene sulfonate. The amount of tin compound in these electrolyte compositions is typically an amount that provides a tin content in the range of 5 to 150 g/L. Mixtures of tin compounds may be used in an amount as described above.

The electrolyte useful in the present invention may be alkaline or acidic. Typically the electrolyte is acidic. Suitable acidic electrolytes include, but are not limited to: sulfuric acid, acetic acid, fluoroboric acid, alkanesulfonic acids such as methanesulfonic acid, ethanesulfonic acid, propanesulfonic acid and trifluoromethane sulfonic acid, arylsulfonic acids such as benzenesulfonic acid and p-toluene sulfonic acid, sulfamic acid, hydrochloric acid, hydrobromic acid, perchloric acid, nitric acid, chromic acid and phosphoric acid. Mixtures of acids may be advantageously used in the present metal plating baths. Preferred acids include sulfuric acid, methanesulfonic acid, ethanesulfonic acid, propanesulfonic acid, hydrochloric acid and mixtures thereof. The acids may be present in an amount in the range of from 1 to 400 g/L. Electrolytes are generally commercially available from a variety of sources and may be used without further purification.

Such electrolytes may optionally contain a source of halide ions. Typically chloride ions are used. Exemplary chloride ion sources include copper chloride, tin chloride, sodium chloride and hydrochloric acid. A wide range of halide ion concentrations may be used in the present invention. Typically, the halide ion concentration is in the range of from 0 to 100 ppm based on the plating bath. Such halide ion sources are generally commercially available and may be used without further purification.

The plating compositions preferably contain an accelerator. Any accelerators (also referred to as brightening agents) are suitable for use in the present invention. Such accelerators are well-known to those skilled in the art. Accelerators include, but are not limited to, N,N-dimethyl-dithiocarbamic acid-(3-sulfopropyl)ester; 3-mercapto-propylsulfonic acid-(3-sulfopropyl)ester; 3-mercapto-propylsulfonic acid sodium salt; carbonic acid-dithio-o-ethylester-s-ester with 3-mercapto-1-propane sulfonic acid potassium salt; bis-sulfopropyl disulfide; bis-(sodium sulfopropyl)-disulfide; 3-(benzothiazolyl-s-thio)propyl sulfonic acid sodium salt; pyridinium propyl sulfobetaine; 1-sodium-3-mercaptopropane-1-sulfonate; N,N-dimethyl-dithiocarbamic acid-(3-sulfoethyl)ester; 3-mercapto-ethyl propylsulfonic acid-(3-sulfoethyl)ester; 3-mercapto-ethylsulfonic acid sodium salt; carbonic acid-dithio-o-ethylester-s-ester with 3-mercapto-1-ethane sulfonic acid potassium salt; bis-sulfoethyl disulfide; 3-(benzothiazolyl-s-thio)ethyl sulfonic acid sodium salt; pyridinium ethyl sulfobetaine; and 1-sodium-3-mercaptoethane-1-sulfonate. Accelerators may be used in a variety of amounts. In general, accelerators are used in an amount of 0.1 ppm to 1000 ppm. Preferably, the accelerator concentration is in the range of 0.5 ppm to 100 ppm. More preferably, the accelerator concentration is in the range of 0.5 ppm to 50 ppm, and most preferably, in the range of 0.5 ppm to 25 ppm.

Any compound capable of suppressing the metal plating rate may be used as a suppressor in the present electroplating compositions. Suitable suppressors include, but are not limited to, polypropylene glycol copolymers and polyethylene glycol copolymers, including ethylene oxide-propylene oxide ("EO/PO") copolymers and butyl alcohol-ethylene oxide-propylene oxide copolymers. Suitable butyl alcohol-ethylene oxide-propylene oxide copolymers are those having a weight average molecular weight of 100 to 100,000, preferably 500 to 10,000. When such suppressors are used, they are typically present in an amount in the range of from 1 to 10,000 ppm based on the weight of the composition, and more typically from 5 to 10,000 ppm.

In general, the reaction products have a number average molecular weight (Mn) of 200 to 10,000, typically from 300 to 50,000, preferably from 500 to 8000, although reaction products having other Mn values may be used. Such reaction products may have a weight average molecular weight (Mw) value in the range of 1000 to 50,000, typically from 5000 to 30,000, although other Mw values may be used.

The amount of the reaction product (leveling agent) used in the metal electroplating compositions depends upon the particular leveling agents selected, the concentration of the metal ions in the electroplating composition, the particular electrolyte used, the concentration of the electrolyte and the current density applied. In general, the total amount of the leveling agent in the electroplating composition ranges from 0.01 ppm to 5,000 ppm based on the total weight of the plating composition, although greater or lesser amounts may be used. Preferably, the total amount of the leveling agent is from 0.1 to 1000 ppm, more preferably, from 0.1 to 500 ppm, most preferably, from 0.1 to 100 ppm. In addition to their leveling activity, the reaction products may also function as suppressors.

The electroplating compositions may be prepared by combining the components in any order. It is preferred that the inorganic components such as source of metal ions, water, electrolyte and optional halide ion source are first added to the bath vessel followed by the organic components such as leveling agent, accelerator, suppressor, and any other organic component.

The electroplating compositions may optionally contain two or more leveling agents. Such additional leveling agents may be another leveling agent of the present invention, or alternatively, may be any conventional leveling agent. Suitable conventional leveling agents that can be used in combination with the present leveling agents include, without limitations, those disclosed in U.S. Pat. No. 6,610,192 to Step et al., U.S. Pat. No. 7,128,822 to Wang et al., U.S. Pat. No. 7,374,652 to Hayashi et al. and U.S. Pat. No. 6,800,188 to Hagiwara et al. Such combination of leveling agents may be used to tailor the characteristics of the plating bath, including leveling ability and throwing power.

Typically, the plating compositions may be used at any temperature from 10 to 65° C. or higher. Preferably, the temperature of the plating composition is from 10 to 35° C. and more preferably, from 15 to 30° C.

In general, the metal electroplating compositions are agitated during use. Any suitable agitation method may be used and such methods are well-known in the art. Suitable agitation methods include, but are not limited to air sparging, work piece agitation, and impingement.

Typically, a substrate is electroplated by contacting the substrate with the plating composition. The substrate typically functions as the cathode. The plating composition contains an anode, which may be soluble or insoluble. Potential is typically applied to the electrodes. Sufficient current density is applied and plating performed for a period of time sufficient to deposit a metal layer having a desired thickness on the substrate as well as fill blind vias, trenches and through-holes or to conformally plate through-holes. Current densities include, but are not limited to, the range of 0.05 to 10 A/dm$^2$, although higher and lower current densities may be used. The specific current density depends in part upon the substrate to be plated, the composition of the plating bath and the desired surface metal thickness. Such current density choice is within the abilities of those skilled in the art.

An advantage of the present invention is that substantially level metal deposits are obtained on a PCB and other substrates. By "substantially level" metal layer is meant that the step height, i.e., the difference between areas of dense very small apertures and areas free of or substantially free of apertures, is less than 5 um, and preferably, less than 1 um. Through-holes and/or blind vias in the PCB are substantially filled. A further advantage of the present invention is that a wide range of apertures and aperture sizes may be filled.

Throwing power is defined as the ratio of the average thickness of the metal plated in the center of a through-hole compared to the average thickness of the metal plated at the surface of the PCB sample and is reported as a percentage. The higher the throwing power, the better the plating composition is able to conformally plate the through-hole. Metal plating compositions of the present invention may have a throwing power of >65%, preferably, >70%.

The compounds provide metal layers having a substantially level surface across a substrate, even on substrates having small features and on substrates having a variety of feature sizes. The plating methods effectively deposit metals in through-holes and blind via holes such that the metal plating compositions have good throwing power and reduced cracking.

While the methods of the present invention have been generally described with reference to printed circuit board manufacture, it is appreciated that the present invention may be useful in any electrolytic process where an essentially level or planar metal deposit and filled or conformally plated apertures are desired. Such processes include, but are not limited to semiconductor packaging and interconnect manufacture.

The following examples are intended to further illustrate the invention but are not intended to limit its scope.

EXAMPLE 1

2,4-Dichloropyrimidine (14.7 g, 0.1 mol) in 20 mL isopropanol was heated to 80° C. in a 100 mL round-bottom, three-neck flask equipped with condenser, thermometer, and stir bar. 4,7,10-Trioxa-1,13-tridecanediamine (22 g, 0.1 mol) was added dropwise to the solution, and the heating bath temperature was increased to 95° C. The resulting mixture was heated for 4 hours, then left to stir at room temperature overnight. The molar ratio of the pyrimidine moiety to the diamine moiety was 1:1 based on monomer molar ratios.

Ten additional reaction products were prepared using substantially the same procedure as described above except the molar ratios and reactants differed. Table 1 below discloses the reactants for each reaction product and the molar ratio of each reactant.

TABLE 1

| Reaction Product | Halogenated Pyrimidine Derivative ($M_1$) | Polyamine ($M_2/M_3$) | Molar Ratio ($M_1$:$M_2$ or $M_1$:$M_2$:$M_3$) |
|---|---|---|---|
| 1 | 2,4-dichloropyrimidine | H$_2$N~~O~~O~~O~~NH$_2$ | 1:1 |
| 2 | 2,4-dichloropyrimidine | H$_2$N~~O~~O~~O~~NH$_2$ | 1:2 |

TABLE 1-continued

| Reaction Product | Halogenated Pyrimidine Derivative (M₁) | Polyamine (M₂/M₃) | Molar Ratio (M₁:M₂ or M₁:M₂:M₃) |
|---|---|---|---|
| 3 | 2,4-dichloropyrimidine | H₂N−CH₂CH₂−O−CH₂CH₂−O−CH₂CH₂−NH₂ | 1:1 |
| 4 | 2,4-dichloropyrimidine | H₂N−CH₂CH₂−O−CH₂CH₂−O−CH₂CH₂−NH₂ | 1:0.7 |
| 5 | 6-amino-2,4-dichloropyrimidine | H₂N−(CH₂)₃−O−CH₂CH₂−O−CH₂CH₂−O−(CH₂)₃−NH₂ | 1:1 |
| 6 | 2,4-dichloropyrimidine | H₂N−(CH₂)₃−O−CH₂CH₂−O−CH₂CH₂−O−(CH₂)₃−NH₂<br>H₂N−CH₂CH₂−O−CH₂CH₂−O−CH₂CH₂−NH₂ | 1:1:1 |
| 7 | 2,4-dichloro-6-methylpyrimidine | H₂N−(CH₂)₃−O−CH₂CH₂−O−CH₂CH₂−O−(CH₂)₃−NH₂ | 1:1 |
| 8 | 2,4-dichloropyrimidine | H₂N−[CH(CH₃)CH₂−O]₂.₅−CH(CH₃)−NH₂ | 1:1 |
| 9 | 2,4-dichloropyrimidine | H₂N−[CH(CH₃)CH₂−O]₆.₁−CH(CH₃)−NH₂ | 1:1 |
| 10 | 2,4-dichloropyrimidine | branched polyetheramine with x, y, z arms, NH₂ terminated; x + y + z = 5–6 | 1:0.667 |
| 11 | 2,4-dichloropyrimidine | H₂N−(CH₂)₃−O−CH₂CH₂−O−CH₂CH₂−O−(CH₂)₃−NH₂<br>H₂N−[CH(CH₃)CH₂−O]₂.₅−CH(CH₃)−NH₂ | 1:0.5:0.5 |

EXAMPLE 2

Copper electroplating baths were prepared by combining 75 g/L copper as copper sulfate pentahydrate, 240 g/L sulfuric acid, 60 ppm chloride ion, 1 ppm or 3 ppm of a brightener and 1.5 g/L of a suppressor. The brightener was bis-(sodium sulfopropyl)-disulfide. The suppressor was an EO/PO copolymer having a weight average molecular weight of <5,000 and terminal hydroxyl groups. Each electroplating bath also contained one of the eleven reaction products from Example 1 in amounts from 0.01-100 ppm as shown in Table 2 below in Example 3. The reaction products were used without purification.

EXAMPLE 3

Samples of 1.6 mm thick of double-sided FR4 PCBs 5 cm×9.5 cm having through-holes were plated in a Haring cell using the copper plating baths of Example 2. The 1.6 mm thick samples had 0.25 mm diameter through-holes. The temperature of each bath was 25° C. A current density of 3.24 A/dm² was applied to the 1.6 mm samples for 44 minutes. In addition to the 1.6 mm thick samples, three 3.2 mm thick double-sided FR4 PCBs 5 cm×9.5 cm having 0.3 mm diameter through-holes were plated with copper electroplating baths which included reaction product 2. The temperature of the baths was 25° C. The current density was 2.16 A/dm² and plating was done for 80 minutes. The copper plated samples were analyzed to determine the throwing power ("TP") of the plating baths and percent cracking according to the methods described below.

Throwing power was calculated by determining the ratio of the average thickness of the metal plated in the center of a through-hole compared to the average thickness of the metal plated at the surface of the PCB sample and is reported in Table 2 as a percentage.

The percent cracking was determined according to the industry standard procedure, IPC-TM-650-2.6.8. Thermal Stress, Plated-Through Holes, published by IPC (Northbrook, Ill., USA), dated May, 2004, revision E. The lower the percentage of cracking, the better was the plating bath performance.

Plating bath performance was evaluated by throwing power and cracking. Table 2 shows that the majority of the samples plated had throwing power which exceeded 65% and many exceeded the preferred 70%.

TABLE 2

| Reaction Product | Panel Thickness | Leveler Conc., ppm | Brightener Conc., ppm | TP % | Cracking % |
|---|---|---|---|---|---|
| 1 | 1.6 | 1 | 1 | 71 | 0 |
|   | 1.6 | 5 | 1 | 81 | 0 |
|   | 1.6 | 10 | 1 | 80 | 0 |
|   | 1.6 | 20 | 1 | 85 | 0 |
| 2 | 1.6 | 1 | 1 | 72 | 0 |
|   | 1.6 | 5 | 1 | 74 | 0 |
|   | 1.6 | 10 | 1 | 79 | 0 |
|   | 1.6 | 20 | 1 | 85 | 0 |
|   | 3.2 | 20 | 1 | 63 | 0 |
|   | 3.2 | 50 | 1 | 65 | 0 |
|   | 3.2 | 100 | 1 | 75 | 0 |
| 3 | 1.6 | 5 | 3 | 85 | 0 |
|   | 1.6 | 10 | 3 | 77 | 0 |
|   | 1.6 | 20 | 3 | 75 | 0 |
| 4 | 1.6 | 1 | 1 | 73 | 0 |
|   | 1.6 | 5 | 1 | 78 | 0 |
|   | 1.6 | 10 | 1 | 76 | 0 |
|   | 1.6 | 20 | 1 | 81 | 60 |
| 5 | 1.6 | 10 | 1 | 71 | 0 |
|   | 1.6 | 20 | 1 | 80 | 0 |
|   | 1.6 | 50 | 1 | 74 | 0 |
|   | 1.6 | 100 | 1 | 76 | 0 |
| 6 | 1.6 | 1 | 1 | 72 | 0 |
|   | 1.6 | 5 | 1 | 85 | 0 |
|   | 1.6 | 10 | 1 | 78 | 0 |
|   | 1.6 | 20 | 1 | 80 | 0 |
| 7 | 1.6 | 1 | 1 | 85 | 0 |
|   | 1.6 | 5 | 1 | 21 | 0 |
|   | 1.6 | 10 | 1 | 78 | 0 |
|   | 1.6 | 20 | 1 | 77 | 0 |
| 8 | 1.6 | 1 | 1 | 72 | 0 |
|   | 1.6 | 5 | 1 | 86 | 0 |
|   | 1.6 | 10 | 1 | 86 | 10 |
|   | 1.6 | 20 | 1 | 92 | 48 |
| 9 | 1.6 | 1 | 1 | 72 | 0 |
|   | 1.6 | 5 | 1 | 83 | 0 |
|   | 1.6 | 10 | 1 | 88 | 15 |
|   | 1.6 | 20 | 1 | 87 | 10 |
| 10 | 1.6 | 0.01 | 1 | 70 | 0 |
|   | 1.6 | 0.05 | 1 | 80 | 0 |
|   | 1.6 | 0.1 | 1 | 79 | 10 |
|   | 1.6 | 0.2 | 1 | 84 | 50 |
| 11 | 1.6 | 1 | 1 | 80 | 0 |
|   | 1.6 | 5 | 1 | 76 | 0 |
|   | 1.6 | 10 | 1 | 76 | 0 |

What is claimed is:

1. A metal electroplating composition comprising: one or more sources of metal ions chosen from copper salts and tin salts, and one or more compounds of a reaction product of one or more compounds having formula:

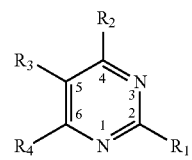

(I)

wherein $R_1$, $R_2$, $R_3$ and $R_4$ are the same or different and are hydrogen, or halogen, or linear or branched, substituted or unsubstituted $(C_1$-$C_{10})$alkyl, or —$NR_5R_6$ wherein $R_5$ and $R_6$ are the same or different and are hydrogen, or linear or branched, substituted or unsubstituted $(C_1$-$C_{10})$ alkyl, or $(C_1$-$C_{10})$alkoxy, or mercaptan, or mercapto$(C_1$-$C_{10})$alkyl, or —$NO_2$, or —NO, or nitro$(C_1$-$C_{10})$alkyl, or $R_3$ and $R_4$ can be taken together with all of their carbon atoms to form a substituted or unsubstituted aryl, and with the proviso that at least one of $R_1$, $R_2$, $R_3$ and $R_4$ is a halogen; and one or more compounds having formula:

$$Y_1-R-Y_2 \qquad (II)$$

wherein $Y_1$ and $Y_2$ are the same or different and are chosen from hydrogen, —$NH_2$, —SH, or —OH,
R is a moiety having formula:

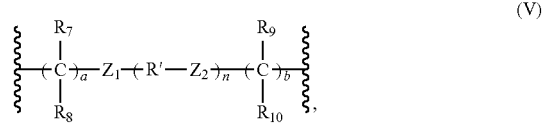

(V)

and wherein $Z_1$ and $Z_2$ of moiety (V) may be the same or different and are chosen from:

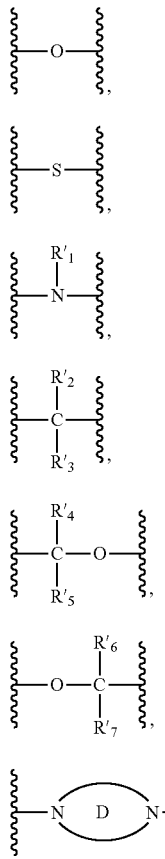

(VII)

(VIII)

(IX)

(X)

(XI)

(XII)

(XIII)

wherein D is substituted or unsubstituted $(C_5-C_{12})$cycloalkyl or $(C_5-C_{12})$aryl, R' of moiety (V) is a moiety having formula:

(XIV)

wherein $R_7$ through $R_{10}$ are the same or different and are chosen from hydrogen, or linear or branched $(C_1-C_5)$ alkyl, or linear or branched amino$(C_1-C_5)$alkyl, or hydroxyl, or linear or branched hydroxy$(C_1-C_5)$alkyl; $R'_1$ through $R'_7$ are the same or different and are chosen from hydrogen, or linear or branched $(C_1-C_5)$alkyl, or hydroxyl, or linear or branched hydroxy$(C_1-C_5)$ alkyl, or linear or branched amino$(C_1-C_5)$alkyl; $R'_8$ and $R'_9$ are the same or different and are chosen from hydrogen, or linear or branched $(C_1-C_5)$alkyl, or hydroxyl, or hydroxy$(C_1-C_5)$ alkyl, or a moiety having formula:

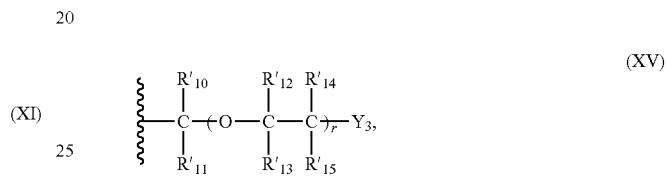

(XV)

wherein $R'_{10}$ through $R'_{15}$ are the same or different and are chosen from hydrogen, or linear or branched $(C_1-C_5)$ alkyl; $Y_3$ is —$NH_2$, —SH or —OH; a, b, e and n are integers of 1 to 20 and r is 1 to 10.

2. The metal electroplating composition of claim 1, further comprising one or more accelerators.

3. A method comprising:
 a) contacting a substrate to be metal plated with the metal electroplating composition of claim 1;
 b) applying a current; and
 c) electroplating metal on the substrate.

4. The method of claim 3, wherein the substrate comprises a plurality of through-holes and vias.

* * * * *